United States Patent [19]

Veiro et al.

[11] Patent Number: 5,525,232
[45] Date of Patent: Jun. 11, 1996

[54] METHOD FOR ENTRAPMENT OF CATIONIC SPECIES IN LEMELLAR VESICLES

[75] Inventors: Jeffrey A. Veiro, Midlands, England; Ajoy C. Chakrabarti; Pieter R. Cullis, both of Vancouver, Canada

[73] Assignee: The Liposome Company, Inc., Princeton, N.J.

[21] Appl. No.: 137,371

[22] Filed: Oct. 14, 1993

Related U.S. Application Data

[63] Continuation of Ser. No. 487,734, Mar. 2, 1990, abandoned.
[51] Int. Cl.$^6$ .................................................. B01D 61/38
[52] U.S. Cl. ........................................... 210/638; 210/643
[58] Field of Search ..................................... 210/638, 643, 210/500, 21, 639; 424/498, 422; 435/94; 436/829

[56] References Cited

U.S. PATENT DOCUMENTS

| | | | |
|---|---|---|---|
| 4,235,871 | 11/1980 | Papahadjopoulos et al. | 424/19 |
| 4,581,222 | 4/1986 | Baldeschwieler et al. | 436/517 X |
| 4,728,575 | 3/1988 | Gamble et al. | 428/402.2 |

FOREIGN PATENT DOCUMENTS

| | | |
|---|---|---|
| 85/04578 | 10/1985 | WIPO . |
| 86/00238 | 1/1986 | WIPO . |
| 86/01102 | 2/1986 | WIPO . |
| 87/00043 | 1/1987 | WIPO . |
| 87/02219 | 4/1987 | WIPO . |

OTHER PUBLICATIONS

Bangham, et al., "Diffusion of Univalent Ions across the Lamellae of Swollen Phospholipids,", 1965, J. Mol. Biol. 13:238–252.

Deamer, et al., "Liposome Preparation: Methods and Mechanisms", 1983, Marc Ostro Ed., Marcel Dekker, Inc., NY pp. 27–51.

Fiske, et al., "The Colorimetric Determination of Phosphorus", 1925, J. Biol. Chem., 66(2):375–400.

Hope, et a., "Production of large unilamellar vesicles by a rapid extrusion procedure. Characterization of size distribution, trapped volume and ability to maintain a membrane potential", 1985, BBA, 812:55–65.

Hope, et al., "Lipid Asymmetry Induced by Transmembrane pH Gradients in Larg e Unilamellar Vesicles", 1987, J. Biol. Chem., 262(9):4360–4367.

Hunt, et al., "Lanthanide–ion transport across phospholipid vesicular membranes: a comparison of alamethicin 30 and A23187 using $^1$H–NMR spectroscopy", 1982, Bio. Sci, Rep. 2:921–928.

Hwang, et al., "Encapsulation, with high efficiency of radioactive metal ions in liposomes", 1982, BBA 716:101–109.

Hyono, et al., "Movement of calcium through artificial lipid membranes and the effects of ionophores":, 1975, BBA 389:34–46.

Kolber, et al., "Fluorescence Study of the Divalent Cation–Transport Mechanism of Ionophore A231187 in Phospholipid Membranes":, 1981, Biophys. J. 36:369–391.

(List continued on next page.)

Primary Examiner—Frank Spear
Attorney, Agent, or Firm—Kenneth B. Rubin

[57] ABSTRACT

Methods are disclosed for entrapment of a cation in a vesicle having a membrane and an acidic aqueous compartment comprising contacting the vesicle with a buffer solution comprising the cation and a lipophilic, carboxylic ionophoretic antibiotic capable of complexing with the cation and increasing the cation's permeability across the vesicle membrane, wherein there is a pH gradient between the acidic aqueous compartment and the buffer solution. The cation can be for example iron or calcium and the ionophore A23187. The pH gradient can be established across the bilayer by a relatively acidic or basic intravesicular aqueous compartment of the unilamellar vesicle and the buffer solution and the cation loads via the pH gradient. The invention also contemplates a unilamellar vesicle comprising an aqueous compartment including a cationic species in a concentration between 100 mM and 500 mM.

15 Claims, 10 Drawing Sheets

OTHER PUBLICATIONS

Mauk, et al., "Preparation of Lipid Vesicles Containing High Levels of Entrapped Radioactive Cations", 1979, Anal. Biochem. 94:302–307.

Mayer, et al., "Influence of Ion Gradients on the Transbilayer Distribution of Dibucaine in Large Unilamellar Vesicles", 1988, Biochem. 27:2053–2060.

Pfeiffer, et al., "Ionophore A23187: The Effect of H+ Concentration on Complex Formation with Divalent and Monovalent Cations and the Demonstration of K+ Transport in Mitochondria Mediated by A23187", 1976, Biochem. 15(5):935–943.

Papahadjopoulos, et al., "Phospholipid Model Membranes I. Structural Characteristics of Hydrated Liquid crystals":, 1967, BBAS 135:624–638.

Pippard, et al., "Simple Assay for Urinary Iron after Desferrioxamine Therapy", Mar. 1982, A.J.C.P. 324–327.

Reed, et al., "A Divalent Cation Ionophore":, ;1972, J. Biol. Chem. 247(21):6970–6977.

Skehel, et al., "Studies on the Primary Structure of the Influenza Virus Hemagglutinin", 1975, Proc. Nat. Acad. Sci, 72(1):93–97.

Szoka, "Comparative properties and methods of preparation of Lipid Vesicles(Liposomes)":, 1980, Ann. Rev. Biophys. Bioeng. 9:467–508.

Turner, et al., "In–111–labeled Liposomes: Dosimetry and tumor Depiction", 1988, 166:761–765.

Young, et al., "Mobile carrier ionophores for Fe(II),", BBA 469:281–291.

METHOD FOR ENTRAPMENT OF CATIONIC SPECIES IN LEMELLAR VESICLES

This is a continuation of application Ser. No. 07/487,734 filed on Mar. 2, 1990, now abandoned.

BACKGROUND OF THE INVENTION

The present invention relates to a method of encapsulating cationic species in liposomes and, more particularly, to a method of encapsulating high concentrations of cationic species in unilamellar and multilamellar vesicles.

Liposome vesicles are completely closed lipid bilayer membranes containing an entrapped aqueous volume. Liposomes may be unilamellar vesicles (possessing a single membrane bilayer) or multilameller vesicles (onion-like structures characterized by two or more membrane bilayers, each separated from the next by an aqueous layer). The bilayer is composed of two lipid monolayers having a hydrophobic "tail" region and a hydrophilic "head" region. The structure of the membrane bilayer is such that the hydrophobic (nonpolar) "tails" of the lipid monolayers orient towards the center of the bilayer while the hydrophilic "heads" orient towards the aqueous phase.

The original liposome preparation of Bangham et al. (J. Mol. Biol., 1965, 12:238–252 involves suspending phospholipids in an organic solvent which is then evaporated to dryness leaving a phospholipid film on the reaction vessel. Next, an appropriate amount of aqueous phase is added, the mixture is allowed to "swell," and the resulting liposomes which consist of multilamellar vesicles (MLVs) are dispersed by mechanical means. This technique provides the basis for the development of the small sonicated unilamellar vesicles described by Papahadjopoulos et al. (Biochim. Biophys. Acta., 1968, 135:624–638).

An ability to encapsulate high concentrations of divalent and trivalent cations in the aqueous compartment of a liposome, such as LUVs, has many potential applications. For example, encapsulation of gamma-emitting radionucleotides such as gadolinium ($^{153}Gd^{3+}$), gallium ($^{67}Ga^{3+}$), and indium ($^{111}In^{3+}$) may be used for contrast enhanced nuclear magnetic resonance imaging and determining the biodistribution of liposomes in vivo, Turner et al., Radiology, 166, 761–765 (1988). Furthermore, the encapsulation of divalent and trivalent cations such gold ($Au^{3+}$) and iron ($Fe^{++}$) or barium ($Ba^{++}$), in addition to uranium and lead, may be suitable for the preparation of electron dense or "heavy" LUVs which may have utility in electron microscopy studies or liposome/plasma separation procedures.

While the desirability of incorporating high concentrations of cations within the aqueous compartment of LUVs has been recognized, it has proven to be difficult in practice to achieve such high concentrations. In this regard, a number of processes have been proposed. For example, there has been proposed the use of passive entrapment to load the cation into the vesicle. However, such technique has been observed to result in low trapping efficiencies. Hwang et al., PNAS 74, 4991–4995 (1978). The use of lipophilic carboxylic ionophoretic antibiotics such as A23187 has been proposed for increasing the cation permeability of lipid membranes by forming a complex with cations. Reed et al., J. Biological Chemistry 247, 6970–6977 (1972). In effect, such technique increases the solubility of the cations in the lipid phase since the ionophore acts as a cation carrier. Nonetheless, the use of such ionophores as a method of remote cation loading in general results in an equilibrium distribution of the cation. This, of course, translates into entrapment of undesirably low levels of the extravesicular cation. Kolber et al., Biophysics Journal, 36, 369–391.

Techniques have also been developed for encapsulating cationic species into an LUV in amounts greater than achievable under equilibrium conditions. For example, the entrapment of appropriate chelating agents has been found to enable entrapment of higher levels of the cation. Nonetheless, such technique is limited to some extent by the limit in the interior concentration of the chelating agent which can be achieved, which is affected by the specificity of the chelator for the cation being loaded. In certain situations, binding affinities of the chelator have been found not to be stronger than that of the ionophore employed. Hwang, Journal of Nuclear Medicine, 19, 1162–70 (1978); Mauk et al., Analytical Biochemistry, 94, 302–307 (1979); Hwang et al., BBA, 716, 101–109 (1982).

Similar problems have been encountered with multilamellar vesicles (MLVs).

Methods have been disclosed for the entrapment of higher than equilibrium concentrations of ionizable bioactive agents, such as ionizable antineoplastic agents, when the vesicles employed possess a transmembrane concentration gradient (Bally et al., International Publication No. WO 86/01102, published Feb. 27, 1986, entitled "Encapsulation of Antineoplastic Agents in Liposomes"). Such a transmembrane gradient can be established via a sodium-potassium ($Na^+/K^+$) or a pH gradient, gradients which reflect loading of monovalent cartons, $K^+$ or $H^+$. The gradient loads the ionizable drug into the vesicle. The vesicles may additionally but not necessarily contain an ionophore such as valinomycin which aids in the loading of $K^+$ into the vesicles.

The mechanism of this valinomycin-driven loading of $K^+$ is via an ion-for-ion exchange of $Na^+$ for $K^+$, or ion for $H^+$ (in the case of a transmembrane pH gradient) creating an established equilibrium, unlike the mechanism of the instant ionophores. The instant invention loads cartons into vesicles as a result of a transmembrane pH gradient and an ionophore, both of which are required in the practice of the invention, but not as a result of an exchange mechanism.

SUMMARY OF THE INVENTION

In view of the foregoing limitations and shortcomings of prior art techniques for loading cationic species into multilamellar and unilamellar vesicles generally and into an LUV in particular, as well as other disadvantages not specifically mentioned above, it should be apparent that there still exists a need in the art for a method for loading cationic species into such vesicles which is not dependent on an established equilibrium or on the limited solubility of a chelating agent for loading the cationic species therein.

It is, therefore, a primary objective of the present invention to fulfill that need by providing a novel process for loading such cationic species into such vesicles in a high concentration, utilizing an ionophore and a transmembrane pH gradient which, quite unexpectedly, exhibits an ability to significantly increase the ionophoretic activity of a lipophilic carboxylic ionophoretic antibiotic.

More particularly, it is a primary objective of the present invention to provide a process for entrapment of cation in a multilamellar or unilamellar vesicle by creating a transmembrane pH gradient (wherein the intravesicular aqueous compartment is preferably acidic) which acts as the predominant driving force for lipophilic carboxylic ionophoretic antibiotic-mediated accumulation of cation in such aqueous compartment.

It is a further object of the present invention to provide a process for entrapment of a cation in a multilamellar or unilamellar vesicle utilizing a transmembrane pH gradient as driving force wherein intravesicular concentrations of the cationic species are achieved which are over two orders of magnitude greater than the initial extravesicular concentration of the cationic species.

Yet a further object of the invention is to provide a method for the creation of "heavy" liposomes capable of being centrifuged in low speed clinical centrifuges, and for the study via direct observation of liposome-cell interactions, thus enabling tracing the fate of liposomes after entry into living systems. High molecular weight metals such as gold, lead and uranium can be entrapped and separated from cells via centrifugation using the methods of the invention, and can be used in the preparation of heavy liposomes for electron microscopy studies or liposome-plasma separation procedures.

In the "heavy" liposome embodiment of the invention, methods are disclosed for making liposomes via an extrusion method wherein a transmembrane concentration (pH) gradient is formed across the bilayers which additionally comprise an ionophore. Iron cations are loaded via this ionophore and pH gradient into the liposomes.

Briefly described, the aforementioned objects are accomplished according to the present invention by providing, in a first aspect, a method for entrapment of a cation in a vesicle having a membrane and an acidic aqueous compartment comprising contacting the vesicle with a buffer solution comprising the cation and a lipophilic, carboxylic ionophoretic antibiotic capable of complexing with the cation and increasing the cation's permeability across the vesicle membrane, wherein there is a pH gradient between the acidic aqueous compartment and the buffer solution.

The cation can be for example iron or calcium and the ionophore A23187. The pH gradient can be established across the bilayer by a relatively acidic or basic intravesicular aqueous compartment of the unilamellar vesicle and the buffer solution and the cation loads via the pH gradient.

The invention also contemplates a unilamellar vesicle comprising an aqueous compartment including a cationic species in a concentration between 100 mM and 500 mM.

In a more preferred embodiment, the vesicle is a unilamellar vesicle. The intravesicular aqueous compartment is preferably acidic, and has a pH ranging generally between about 3 and 6 and preferably between about 4 and 4.5. The pH gradient which is established is typically above about 3 and preferably between about 3.0 and 3.5.

Advantageously, the ionophoretic antibiotic is A23187, desferrioxamine, ionomycin, X-537A (lasalocid A), or A-204; and the cation is gold, barium, lanthanum, gadolinium, uranium, lead, calcium or iron.

In another aspect, the invention relates to a unilamellar vesicle including an aqueous compartment wherein a cationic species is present in a concentration between about 100 mM and 500 mM.

With the foregoing and other objects, advantages, and features of the invention that will become hereinafter apparent, the nature of the invention may be more clearly understood by reference to the following detailed description of the invention, the appended claims and to the attached drawings.

DETAILED DESCRIPTION OF THE INVENTION

Figure 1:
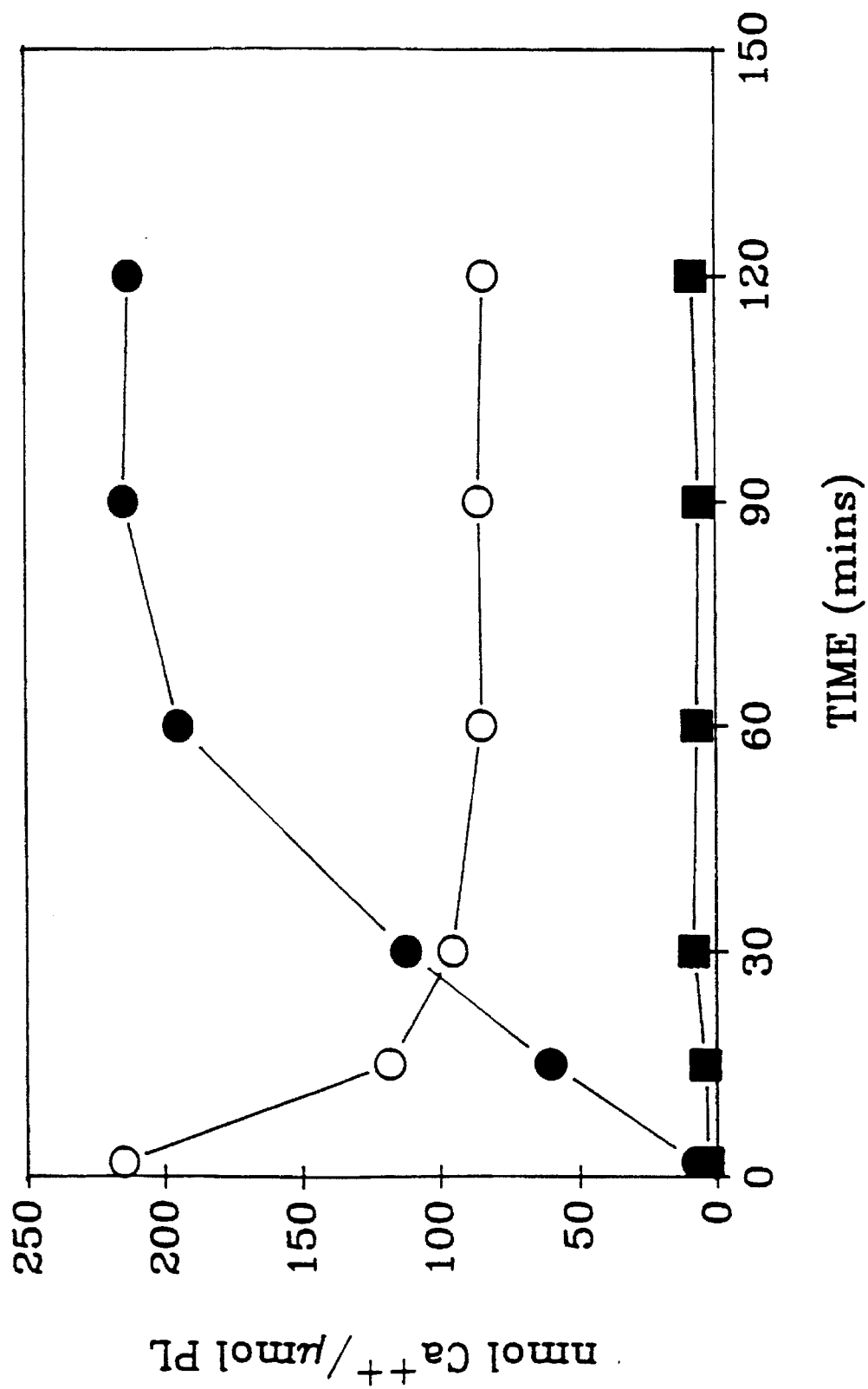
FIG. 1 is a graph depicting the accumulation of $Ca^{++}$ in LUVs exhibiting a pH gradient as a function of time in the presence of 50 ug/ml (open circle), and 0.1 ug/ml (closed circle) of the ionophoretic antibiotic A23187 and in the absence of a pH gradient (closed square)

The following discussion relates specifically to the loading of cationic species into large unilamellar vesicles (LUVs). It will be appreciated, however, that the discussion is also applicable to other vesicle systems such as multilamellar vesicles or single unilamellar vesicles.

The liposome vesicles employed in accordance with the present invention advantageously are large unilamellar vesicles (LUVs) which can be prepared in accordance with techniques well known to persons skilled in the art. For example, LUVs may be prepared from organic solvents or detergents by the injection of lipids solubilized in an organic solvent into an aqueous buffer to cause the spontaneous formation of an LUV. Alternatively, there may be employed the reverse-phase evaporation technique which requires that the lipid be solubilized in organic solvents such as diethyl ether (Papahadjopoulos, U.S. Pat. No. 4,235,871, issued Nov. 25, 1980). Solvent and buffer are combined at specific volume ratios depending upon the organic phase chosen. An emulsion is formed by sonicating mixtures for 15–30 minutes followed by the careful removal of solvent at 400 mmHg pressure until a thick gel has been formed. The gel is collapsed by vortexing or mild sonication and evaporation is continued under a vacuum. The resulting dispersion is often a heterogeneous mixture of oligolamellar and unilamellar vesicles that requires extrusion through polycarbonate filters to achieve relatively homogeneous preparations of unilamellar vesicles. Large unilamellar vesicles can also be formed by solubilizing lipid in an aqueous buffer that contains detergents. A review of all these and other methods for producing liposomes may be found in the text Liposomes, Marc Ostro, ed., Marcel Dekker, Inc., New York, 1983, Chapter 1, the pertinent portions of which are incorporated herein by reference. See also Szoka, Jr. et al., (1980, Ann. Rev. Biophys. Bioeng., 9:467), the pertinent portions of which are also incorporated herein by reference.

More recently, LUVs have been produced by an extrusion procedure wherein a preformed multilamellar vesicle (MLV) is repeatedly extruded under moderate pressures through two stacked polycarbonate filters of 100 nm pore size to result in a relatively homogeneous population of LUVs. A particularly preferred method for forming LUVs is described in Cullis et al., PCT Publication No. 87/00238, Jan. 16, 1986, entitled "Extrusion Technique for Producing Unilamellar Vesicles" incorporated herein by reference. Vesicles made by this technique, called LUVETS, are extruded under pressure through a membrane filter. Vesicles may also be made by an extrusion technique through a 200 nm filter; such vesicles are known as $VET_{200}s$.

According to the present invention, it is preferred to prepare the LUVs by extrusion of frozen and thawed lipid dispersions through 0.1 um polycarbonate filters (Nuclepore) employing an extrusion device (Ltpex Biomembranes, Vancouver). Vesicles prepared in this manner have trapped volumes of 1.5 ul/umol phospholipid employing $^{14}C$ inulin as an aqueous marker, and an average diameter of 90 nm. Reference, in this regard, is made to Bally et al., PCT Publication No. 87/00043, Jan. 15, 1987, entitled "Multilamellar Liposomes Having Improved Trapping Efficiencies" and incorporated herein by reference, and Hope et al., BBA, 812, 55–65 (1985).

In the present invention, the term lipid as used herein shall mean any suitable material resulting in a bilayer such that a hydrophobic portion of the lipid material orients toward the interior of the bilayer while a hydrophilic portion orients toward the aqueous phase. Lipids further include highly hydrophobic components such as triglycerides, sterols such as cholesterol which can be incorporated into a bilayer. The lipids which can be used in the liposome formulations of the present invention are the phospholipids such as phosphatidylcholine (PC), phosphatidylethanolamine (PE), phosphatidylserine (PS), phosphatidylglycerol (PG), phosphatidic acid (PA), phosphatidylinositol (PI), sphingomylin (SPM), and the like, alone or in combination. The phospholipids can be synthetic or derived from natural sources such as egg or soy. The synthetic phospholipids dimyristoylphosphatidylcholine (DMPG) and dimyristoylphosphatidylglycerol (DMPG) may be used. In the preferred embodiments, the phospholipid egg phosphatidylcholine (EPC), is used.

The liposomes can also contain other steroid components such as polyethylene glycol derivatives of cholesterol (PEC-cholesterols), coprostanol, cholestanol, or cholestane, and combinations of EPC and cholesterol. They may also contain organic acid derivatives of sterols such as cholesterol hemisuccinate (CHS), and the like. Organic acid derivatives of tocopherols may also be used as liposome-forming ingredients, such as alpha-tocopherol hemisuccinate (THS). Both CHS- and THS-containing liposomes and their tris salt forms may generally be prepared by any method known in the art for preparing liposomes containing these sterols. In particular, see the procedures of Janoff, et al., PCT Publication No. 85/04578, filed Oct. 24, 1985, entitled "Steroidal Liposomes," and Janoff, et al., PCT Publication No. 87/02219, Apr. 23, 1987, entitled "Alpha-Tocopherol Based Vesicles,". The liposomes may also contain glycolipids. The preferred lipids for use in the invention are egg phosphatidylcholine (EPC) and saturated PCs, advantageously admixed with cholesterol. Especially preferred are EPC in admixture with cholesterol, e.g., at a ratio of 55:45 (EPC::Cholesterol) and the saturated PCs in admixture with cholesterol.

As previously indicated, it is necessary that the aqueous compartment of the LUV be acidic in order to establish the requisite pH gradient between such compartment and a buffer solution containing the cationic species. By "acidic" is meant a pH ranging generally between 3 and 6 and preferably between 4 and 4.5. The upper limit to the pH is determined by the conditions which are physiologically optimal as well as by its effect on the cation binding of the antibiotic. The lower limit of the pH is determined for the most part by the pH at which lipid degradation will occur.

To obtain a vesicle having such acidic compartment, the vesicle may be prepared in the presence of a low pH buffer such as citrate or phosphate having a concentration ranging from about 50 to 500 mM (300 mM citrate is preferable). The extravesicular (external) pH is then raised, either by adding a base or exchanging the external buffer for a buffer with a higher pH. See, for example, Hope, M. J., and Cullis, P. R., *J. Biol. Chem.*, Vol. 262(9) pp. 4360–4366 (1987).

After acidifying the interior compartment of the liposome, it is preferred to remove unentrapped acidic buffer from the LUVs by conventional techniques such as, for example, passing the vesicles through a Sephadex G-50 column pre-equilibrated with the external neutral pH buffer (for example; 150 mM $Na_2SO_4$, 20 mM Hepes, pH 7.4; 300 mM sucrose, 20 mM Hepes, pH 7.4; or 300 mM NaCl, 20 mM Hepes, pH 7.5).

The LUV vesicles having an aqueous acidic interior compartment are next loaded with the cationic species in formulation with the lipophilic ionophore. As previously indicated, there are a number of cationic species which are desirably incorporated into the LUVs including the gamma-emitting radionucleotides, the heavy cations such as gold ($Au^{3+}$), barium ($Ba^{++}$) and iron ($Fe^{++}$) and electron dense cations such as lanthanum ($La^{3+}$). Alkaline earth metal cations such as calcium ($Ca^{3+}$) may also be used. Generally, the technique of the present invention will be applicable to any cationic species which one desires to incorporate into the vesicle and which will both dissolve in the external buffer and form a complex with the ionophore.

The cationic species is formulated in a solution with a lipophilic carboxylic ionophoretic antibiotic which forms a complex with such cationic species and thereby increases the permeability of the lipid membrane for delivery of the cation to the interior of the vesicle. In practice, the desired amount of ionophore in an organic solvent solution is placed into a test tube and the solvent removed, followed by the addition to the tube of an aqueous solution containing the cationic species of interest, for example a buffer system containing $CaCl_2$ where $Ca^{++}$ is to be entrapped.

The specific antibiotic chosen will, of course, depend on the specific cation being loaded in the vesicle. It is preferable to use ionophores with a high cation specificity. Generally, suitable antibiotics are commercially available and include ionophores such as A23187, desferrioxamine, ionomycin, X-537A (lasalocid A), or A-204 which catalyze an electroneutral exchange of protons for cations and which form complexes with cations such as $Ca^{++}$ and $Fe^{++}$. Particularly preferred antibiotics are A23187 and ionomycin, since the specificity of such antibiotic between divalent cations is low. Thus A23187 is capable of transporting divalent cations of a number of transition metals, the cartons of the alkaline earth series, and various trivalent species.

The selected cation/antibiotic combination is next formulated into a solution, such as for example, a buffer solution, for mixing with the LUVs which have an acidic aqueous interior. As previously discussed, the solution is selected such that there will exist a pH gradient between the solution and the interior of the LUV. This is generally achieved by mixing the cationic species and the antibiotic into a buffer solution of suitable pH to establish the desired pH gradient. A person skilled in the art will appreciate that any buffer solution which is generally compatible with the LUVs may be employed. Generally, such solution should have a pH such that a pH gradient of at least about 3 is established, with a pH gradient between 3.0 and 3.5 being preferred. In this regard, standard buffer solutions of higher pH may be employed such as 2- [N-morpholino] ethane-sulfonic acid ("MS") or phosphate. Generally, the buffer should contain between about 0.5 mM and 2.0 mM of the cation and between about 0.1 uM and 20 uM of the antibiotic, the exact amounts depending on the lipid concentration, temperature, and the rate of uptake required. It is noted that lower concentrations of the cationic component, i.e., 0.05 mM to 0.5 mM can give rise to a cationic trapping efficiency of greater than 99% whereas a concentration of 0.5–20 mM significantly decreases the trapping efficiency at a phospholipid concentration of 2.0 mM.

The buffer solution containing the cationic species and the antibiotic is then contacted with the LUVs having the aqueous acidic compartment. Generally, the vesicles themselves will be present as a suspension containing 1.0 mM to 100 mM of the vesicle phospholipid. The buffer and the vesicles are mixed and allowed to interact for a period of time sufficient to allow maximum ionophore mediated cation uptake. The temperature should be maintained above the bilayer gel to liquid crystalline temperature of the lipid being used which is typically between about 20 and 60° C. It has been observed that at elevated temperatures, e.g., of about 60° C., a high cation uptake is possible even where there has been a large reduction in the amount of ionophore.

The data in FIG. 1 indicates that after the initial rapid accumulation of $Ca^{++}$, a time-dependent leakage of the entrapped cation occurred. This efflux is a consequence of A23187 mediated Na+uptake, which would serve to dissipate the internal proton pool via $Na^+$–$H^+$ exchange. While it is generally accepted that the specificity of A23187 for $Na^+$ is significantly less than that of $Ca^{++}$, Pfeiffer and Lardy, *Biochemistry*, 15,935–943 (1976), the relatively high extravesicular $Na^+$a concentration will result in an increased importance of such uptake. If this is indeed true, then it would be expected that the leakage of the $Ca^{++}$ may be overcome by either decreasing the rate of ionophore mediated transport by reducing the concentration of the A23187, or by removing exterior $Na^+$.

The results of the investigation clearly showed that lipophilic ionophoretic antibiotics such as A23187 and transmembrane pH gradients (acidic inside) may be used to achieve a rapid entrapment of cationic species such as $Ca^{++}$, corresponding to essentially 100% sequestration of the extravesicular $Ca^{++}$. Under the conditions employed here this can result in an intravesicular $Ca^{++}$ concentration of over 250 mM and an inside-outside gradient of more than 400-fold. Furthermore, the driving force for cation entrapment was shown not to be chelation via internal titrate but the transmembrane pH gradient.

Without being bound by theory, it is believed that the principle for A23187 mediated $Ca^{++}$ accumulation in response to a pH gradient, is related to the mechanism of action of the ionophores. A23187 possesses a carboxylic acid group and catalyzes an electrically neutral exchange of protons for other cations across the membrane. It is generally accepted that $Ca^{++}$ crosses the membrane complexed with two molecules of A23187, Hyono et al., *BBA* 389, 34–46 (1985); Kolber and Haynes, *Biophisics Journal*, 36, 369–391 (1981); Hunt and Jones, *Biosci. Rep.*, 2, 921–928 (1982). These two molecules of A23187 are present as the carboxylate anion, and so are available to carry two protons or equivalent back across the membrane after releasing the transported divalent cation. This A23187 mediated uptake would be expected to be extremely sensitive to the intravesicular proton pool, where an excess of interior protons will drive ionophore mediated uptake. This is consistent with the results of this study, where reduced transmembrane pH gradients or initial buffering capacities result in reduced uptake levels.

It is interesting to note that A23187 is capable of transporting a wide range of cations, Young and Gomperts, *BBA* 469, 281–291 (1977). Therefore, this method of loading may be used for many cations including $Fe^{++}$, $Au^{3+}$, $Ba^{++}$ and the trivalent radionucleotides. For example, mCi amounts of radionucleotides such as $^{153}Gd^{3+}$ are loaded into the interior of a small concentration of vesicles. Alternatively, $Cu^{3+}$ could be loaded for application in magnetic resonance imaging.

Iron can similarly be entrapped into vesicles by using the ionophore A23187 and a transmembrane pH gradient. Liposomes are made with an internal pH of 4.0 and an external pH of 7.5. The calcium ionophore, A23187, admixed with an aqueous solution such as an aqueous buffer and $FeSO_4$. Uptake occurs upon admixing the LUVs (extruded through 200 nm pore size filter) with the ionophore and $FeSO_4$. In the case of loading $Fe^{3+}$, $FeCl_3$ is employed. However $Fe^{3+}$ loaded only to 20% of the value of $Fe^{++}$, to a captured volume of 47 um cation/umol phospholipid.

"Dense" iron-containing liposomes made by this method could be spun down at 4° C. using 15,000×g in an Eppendorf micro-centrifuge. Table 2 shows the distribution of liposomes which have been centrifuged to pellet the "heavy liposomes." Spinning down of the liposomes after incubation with iron resulted in a visible pellet after 25 minutes at about 15 000×g (using an Eppendorf micro-centrifuge). The pellet and supernatant were easily separated. A large percentage (46.5%) of the total number of liposomes are spun down. Control liposomes (containing no iron) of the same size produced a pellet containing only 15.0% of the total lipid. This value was subtracted from that obtained for the iron-liposomes to calculate the net increase in the percentage of liposomes that pelleted (31.5%).

A second subset of liposomes containing iron that did not spin down existed in the supernatant. These liposomes contained less than half the iron that the spun-down "heavy" liposomes did. Thus, there may exist a critical amount of iron uptake that must be achieved in order to allow for a liposome to spin down. Analysis of liposomes size by a NICOMP particle sizer indicated that the liposomes that spun down were the same size as those that did not (approximately 214 run).

Liposomes extruded through 100 nm pore size filters in the "LUVET" process did not readily spin down in the centrifugation step.

The liposomes of the invention may entrap or be associated with a bioactive agent, i.e. an agent having biological activity, such as for example, a drug, hormone, peptide (e.g., a protein), dye, vitamin, or imaging agent. As used in the present invention, the term bioactive agent is understood to include any compound having biological activity; e.g., drugs and other therapeutic agents such as peptides, hormones, toxins, enzymes, neurotransmitters, lipoproteins, glycoprotein, immunomodulators, immunoglobultns, polysaccharides, cell receptor binding molecules, nucleic acids, polynucleotides, and the like, as well as biological tracer substances such as dyes, radio-opaque agents, and fluorescent agents.

The liposomes resulting from the processes of the present invention can be used therapeutically in mammals, including man, in the treatment of infections or conditions which require the sustained delivery of the drug in its bioactive form.

The mode of administration of the preparation may determine the sites and cells in the organism to which the compound will be delivered. The liposomes of the present invention can be administered alone but will generally be administered in admixture with a pharmaceutical carrier selected with regard to the intended route of administration and standard pharmaceutical practice. The preparations may be injected parenterally, for example, intra-arterially or intravenously. The preparations may also be administered via oral, subcutaneous, or intramuscular routes. For parenteral administration, they can be used, for example, in the form of a sterile aqueous solution which may contain other solutes, for example, salts or glucose. Other uses, depending upon the particular properties of the preparation, may be envisioned by those skilled in the art.

For administration to humans in the curative treatment of disease states responding to drug therapy, the prescribing physician will ultimately determine the appropriate dosage for a given human subject, and this can be expected to vary according to the age, weight, and response of the individual as well as the nature and severity of the patient's disease. The dosage of the drug in liposomal form will generally be about that employed for the free drug. In some cases, however, it may be necessary to administer dosages outside these limits.

The following examples are presented by way of illustration and in no way should be construed as limiting the subject matter disclosed and claimed. Thus, for example, although the examples specifically relate to calcium or iron ions and the ionophoretic antibiotic A23187, it will be appreciated that other ionic species and other lipophilic ionophoretic antibiotics are contemplated. In similar fashion, vesicles other than LUVs are contemplated.

EXAMPLE 1

Enhancement of Calcium Uptake

Egg phosphatidylcholine (EPC) was purchased from Avanti Polar Lipids (Birmingham, Ala.), and used without further purification after verification of purity by thin-layer chromatography. The ionophore A23187 was obtained from Calbiochem (Calgary) and $^{14}C$ methylamine was purchased from New England Nuclear. All other regents were analytical grade or equivalent.

Large unilamellar vesicles were produced by extrusion, Hope et al., *BBA* 812, 55–65 (1985) of frozen and thawed lipid dispersions through 0.1 um polycarbonate filters (Nuclepore) employing an extrusion device (Lipex Biomembranes, Vancouver). Vesicles prepared in this manner had trapped volumes of 1.5 ul/umol phospholipid employing $^{14}C$ inulin as an aqueous marker, and an average diameter of 90 nm. Phospholipid concentrations were determined by analysis of lipid phosphorus as previously described, Fiske and Subbarow, *J. Biol. Chemistry* 66, 375–400 (1925). Vesicles were formed of 50 mg EPC in 2.0 ml citrate buffer pH 4.0.

Transmembrane pH gradients were obtained by preparing the EPC vesicles in the presence of a low pH buffer (300 mM citrate, pH 4 unless stated otherwise). Untrapped buffer was then removed by passing the vesicles through a Sephadex G-50 column pre-equilibrated with the external neutral pH buffer (150 mM $Na_2SO_4$, 20 mM Hepes, pH 7.4 unless stated otherwise).

A known volume of a chloroform stock solution of A23187 was added to a test tube. The solvent was removed under a stream of nitrogen followed by incubation at low pressure. The appropriate extravesicular buffer system containing the cation (for example, $CaCl_2$ and a trace amount of $^{45}Ca$) was added to the test tube (0.15 ml of 0.5 mM $CaCl_2$), and the dispersion mixed thoroughly. To this was added the vesicle suspension (at a concentration of 2 mm phospholipid) at a time which marked the start of the experiment. The final concentration of ionophore in suspension was 50 ug/ml.

Transmembrane pH gradients were determined by measuring the equilibrium transmembrane distribution of the weak base $^{14}C$ methylamine. Methylamine was added to the vesicle system (2 mM phospholipid) to achieve a concentration of 1 uM containing 1 uCi/ml of $^{14}C$ methylamine. At appropriate time intervals aliquots (100 ul) were withdrawn and untrapped probe removed by employing 1 ml Sephadex G-50 mini columns as previously indicated. The trapped probe was determined by liquid scintillation counting employing a Packard 2000CA liquid scintillation counter, and the phospholipid concentration by phosphate assay. Transmembrane pH gradients were calculated according to the equation $pH = \log [MeAM]i/[MeAM]o$, Mayer et al., *Biochemistry* 27, 2053–2060 (1988).

Calcium uptake was monitored by incubating the vesicles in the appropriate buffer containing $CaCl_2$ (0.5 mM unless stated otherwise) containing trace amounts of hu $45Ca(1/Ci/ml)$. Aliquots (100 ul) were withdrawn over a two hour time course and extravesicular $Ca^{++}$ removed by passage over a 1 ml Sephadex G-50 mini column. The vesicles were subsequently analyzed for $^{45}Ca$ and for lipid phosphorus. Experiments were conducted at 23° C. unless stated otherwise.

Initial experiments were designed with the aim of establishing whether a transmembrane pH gradient would affect the ionophoretic activity of A23187. As shown in FIG. 1, the vesicle system experiencing a transmembrane pH gradient (150 mM $Na_2SO_4$, 20 mM Hepes adjusted to pH 7.4 with NaOH outside and 300 mM citrate adjust,ed to pH 4.0 with NaOH inside) exhibited an ability to significantly increase the ionophoretic activity of A23187 (50 ug/ml). Within two minutes $Ca^{++}$ was accumulated to achieve interior levels of 220 mmol $Ca^{++}$/umol phospholipid, or 148 mM (given the trapped volume of 1.5 ul/umol phospholipid), compared to the initial extravesicular $Ca^{++}$ concentration of 0.5 mM. This accumulation is equivalent to more than 99% uptake of the extravesicular cation. Corresponding experiments conducted on vesicular systems experiencing no pH gradients at pH 7.4 inside and outside (FIG. 7) or pH 4.0 inside and out showed only background levels of $Ca^{++}$ uptake (typically less than 5 nmol $Ca^{++}$/umol phospholipid). Experiments conducted on vesicular systems experiencing a reversed pH gradient (inside basic) indicated only background intravesicular $Ca^{++}$ concentrations (<1.0 nmol $Ca^{++}$/umol phospholipid, results not shown).

Figure 2:
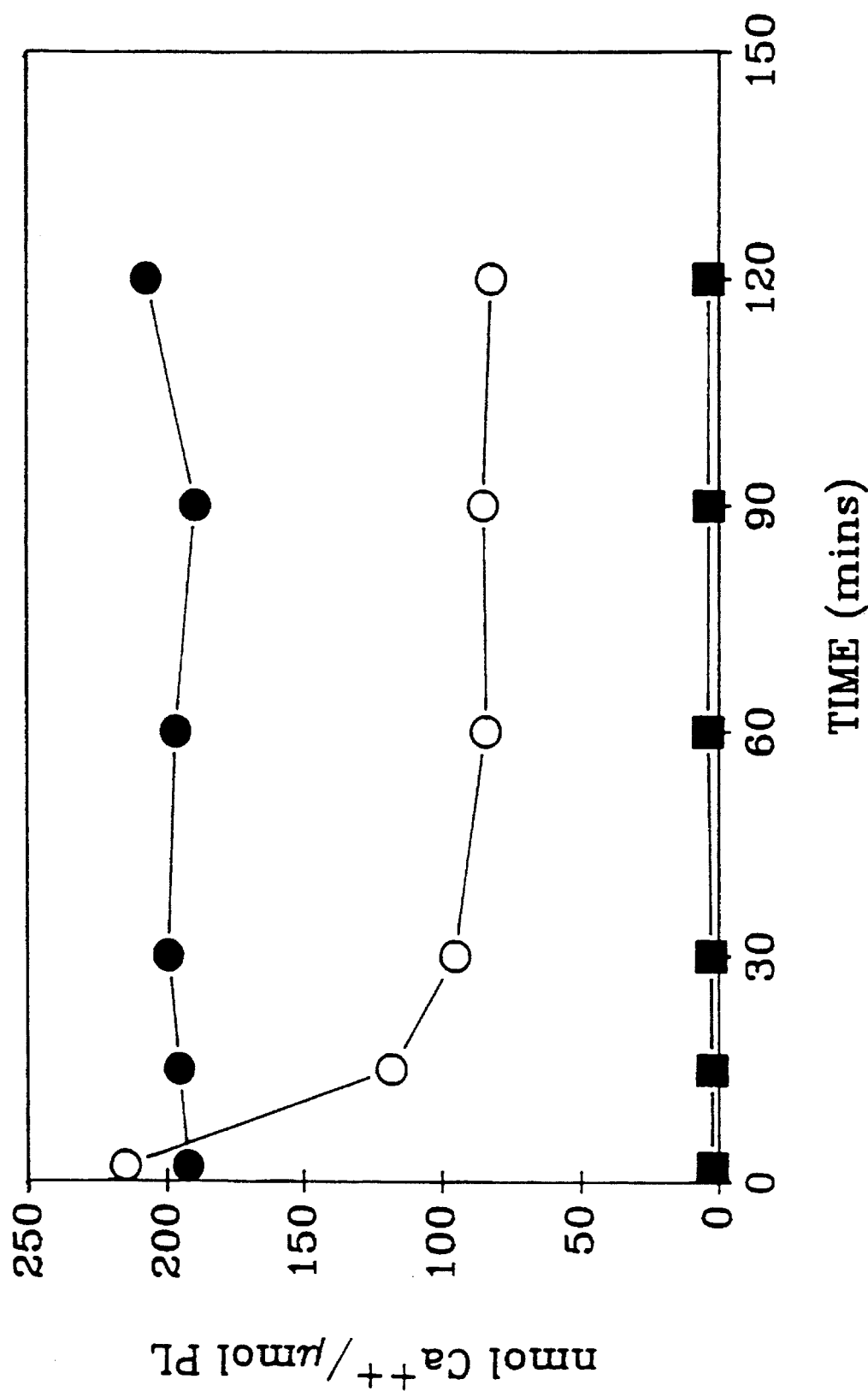
FIG. 2 is a graph depicting the accumulation of $Ca^{++}$ in LUVs as a function of time for a system having a pH gradient and including sodium (open circle), or arginine (closed circle) and for a system having no pH gradient in the presence of arginine (closed square)

Further examination of the data in FIG. 1 indicates that after the initial rapid accumulation of $Ca^{++}$, a time-dependent leakage of the entrapped cation occurred. FIG. 1 shows that by reducing the ionophore concentration to 0.1 ug/ml, the rate of both $Ca^{++}$ influx and efflux were reduced, although it should be noted that greater than 99% entrapment was still achieved. FIG. 2 shows the result of altering the vesicle system used such that no $Na^+$ ions are present. The $Na_2SO_4$ was replaced with sucrose (300 mn) and the intra- and extravesicular pH was adjusted with arginine (free base). As shown in FIG. 2 this system exhibited no significant $Ca^{++}$ leakage after the initial uptake. Consistent with the observations for the $Na^+$ containing vesicle system, the arginine system in the absence of a transmembrane pH gradient indicated no significant cation uptake (FIG. 2).

Figure 3:
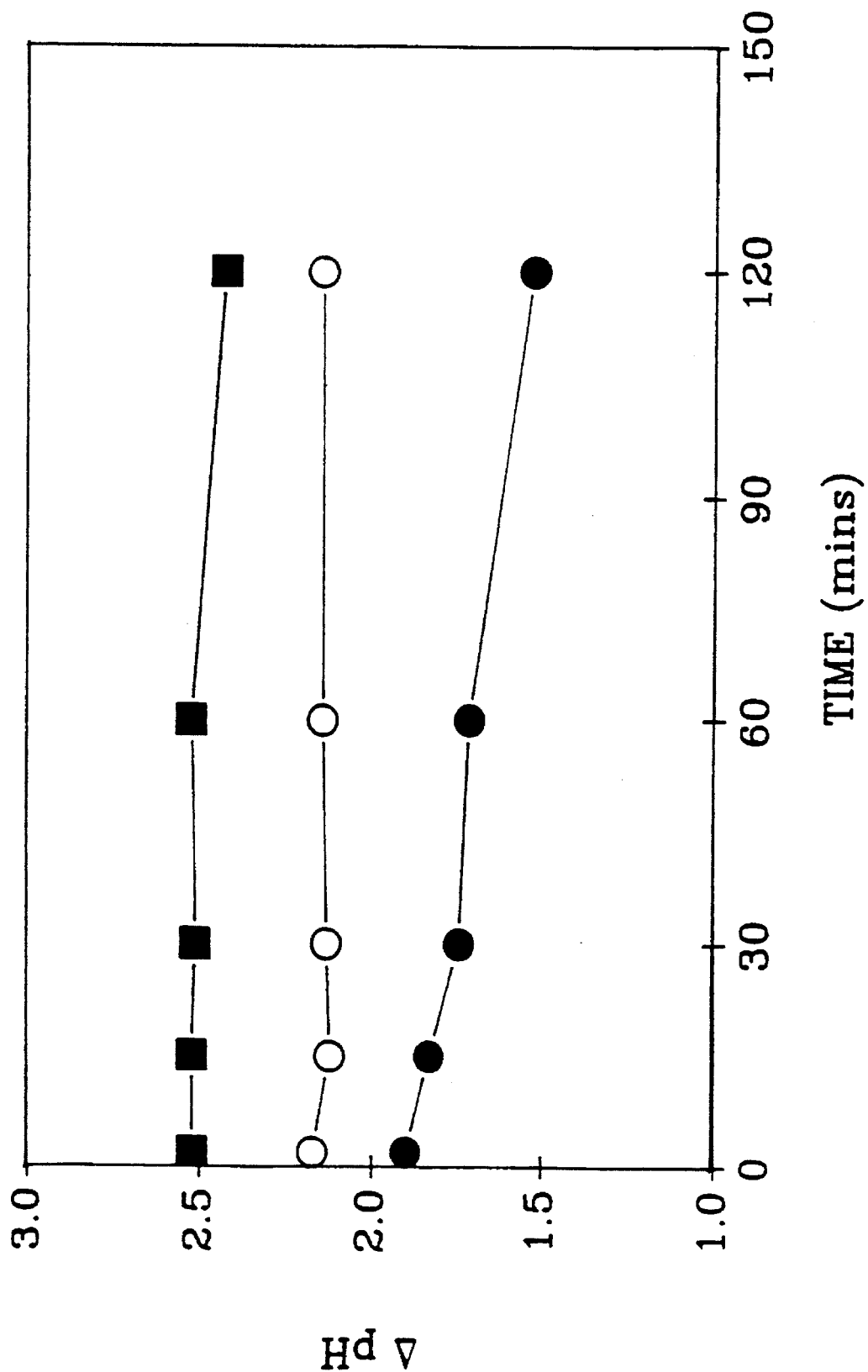
FIG. 3 is a graph depicting the effect on the accumulation of $Ca^{++}$ into LUVs of the transmembrane pH gradient in the absence of ionophore (closed square), in the presence of A23187 and external $Ca^{++}$ for the $Na^+$ vesicle system (closed circle), and the arginine vesicle system (open circle).

In order to show that the dissipation of the transmembrane pH gradient correlated with $Ca^{++}$ efflux, the molecular probe methylamine was used to measure the proton gradient established in the $Na^+$ free and $Na^+$ containing vesicle systems during the time-course of the experiment. As indicated in FIG. 3 the distribution of methylamine for egg PC vesicles in the absence of ionophore ($Na^+$ containing vesicle system) and for the arginine vesicle system in the presence of A23187 (0.1 ug/ml) indicated pH values of 2.5 and 2.2 respectively. These gradients were stable for at least two hours at room temperature (23° C.). However, in the case of the $Na^+$ containing vesicle system in the presence of A23187 (0.1 ug/ml), a time dependent dissipation of the transmembrane pH gradient was observed as $Ca^{++}$ uptake proceeded. In addition, at high A23187 levels (50 ug/ml) (see FIG. 1) no measurable residual pH gradient was detected after two minutes. This leak of residual pH gradient is consistent with the observed efflux of intravesicular $Ca^{++}$ at high ionophore levels.

Figure 4:
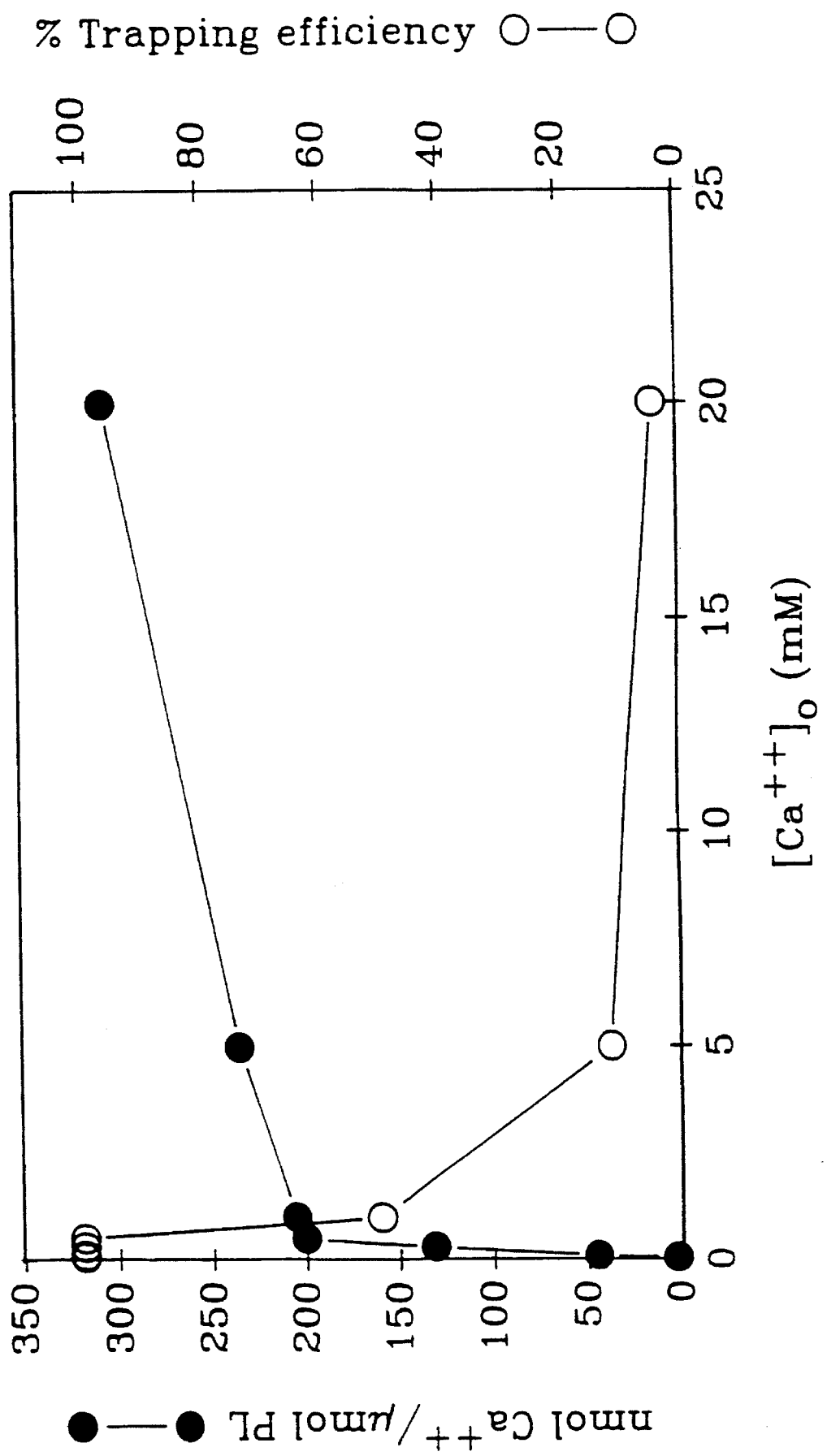
FIG. 4 is a graph depicting the accumulation (closed circle) and percentage trapping efficiency (open circle) into LUVs as a function of the extravesicular $Ca^{++}$ concentration.

The effect of the extravesicular $Ca^{++}$ concentration on the maximum amount of A23187 mediated uptake and the trapping efficiency is depicted in FIG. 4. At low initial extravesicular $Ca^{++}$ concentrations (0.05–0.5 mM), greater than 99% trapping efficiency was observed indicating essentially a complete sequestration of the external $Ca^{++}$ pool. This sequestration corresponds to entrapped $Ca^{++}$ levels of between 2.3 and 200 nmol per umol phospholipid. A residual transmembrane pH gradient was maintained after $Ca^{++}$ uptake as measured by methylamine. However, at higher extravesicular $Ca^{++}$ concentrations (0.5–20 mM), the trapping efficiency significantly decreased and cation uptake plateaued at about 350 nmol Ca /umol phospholipid. Under these experimental conditions no residual pH gradient was detected.

Figure 5:
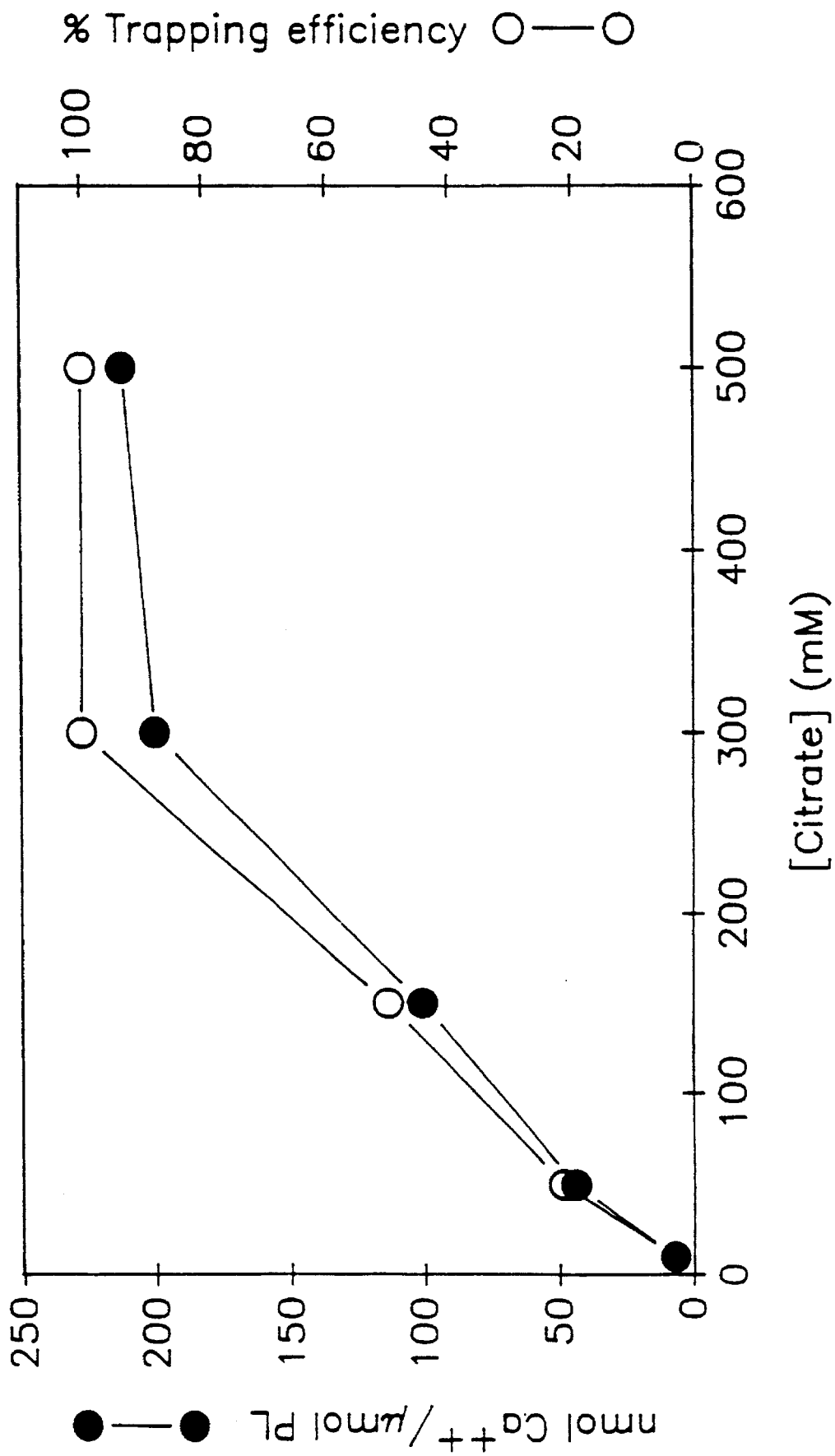
FIG. 5 is a graph depicting $Ca^{++}$ uptake (closed circle) and percentage trapping efficiency (open circle) into LUVs as a function of the internal citrate concentration.
Figure 6:
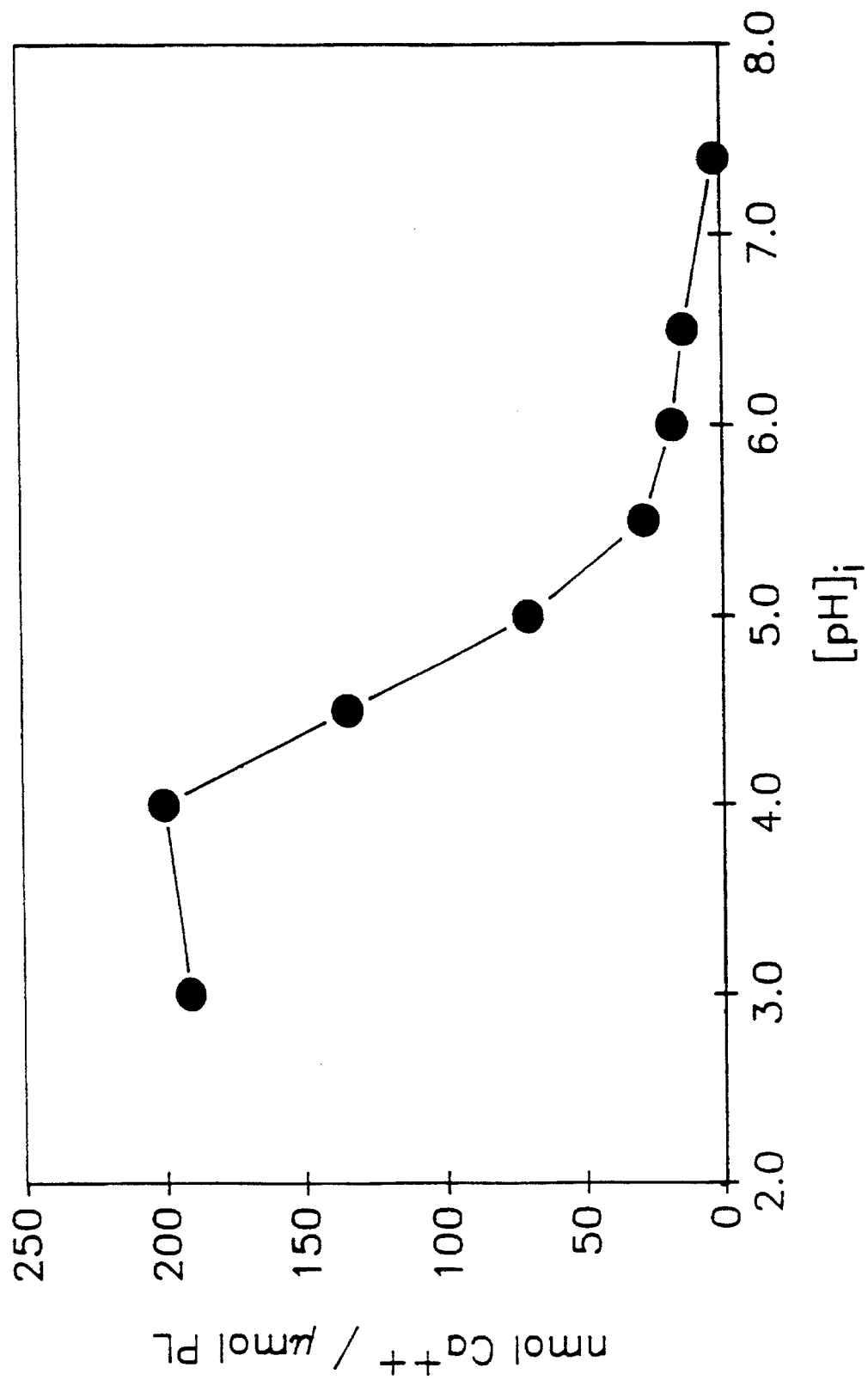
FIG. 6 is a graph depicting mediated $Ca^{++}$ uptake (closed circle) into LUVs as a function of the applied pH differential.

In order to further characterize the transmembrane pH dependent ionophore mediated transport of $Ca^{++}$, the effect of changing the intravesicular buffering capacity at a constant extravesicular $Ca^{++}$ concentration (0 5 mM), on $Ca^{++}$ a uptake was investigated. The data of FIG. 5 indicates that at a low citrate concentration (<300 mM), the buffering capacity appeared to be the limiting factor for maximum ion mediated uptake, and trapping efficiencies approaching 100% were not achieved. Furthermore, no residual transmembrane pH gradient was apparent at the end of the experiment. However, at higher citrate concentrations the extravesicular $Ca^{++}$ became limiting with greater than 99% trapping efficiency, and a residual transmembrane pH gradient of over 2.0 units was still present after uptake. The effect of varying the intravesicular pH at constant outer pH (7.4) on maximum $Ca^{++}$ uptake was also investigated. FIG. 6 shows that as the magnitude of the initial transmembrane pH gradient decreased to below 3.0 pH units, the trapping efficiency was reduced and no residual pH gradient after $Ca^{++}$ uptake was apparent.

Figure 7:
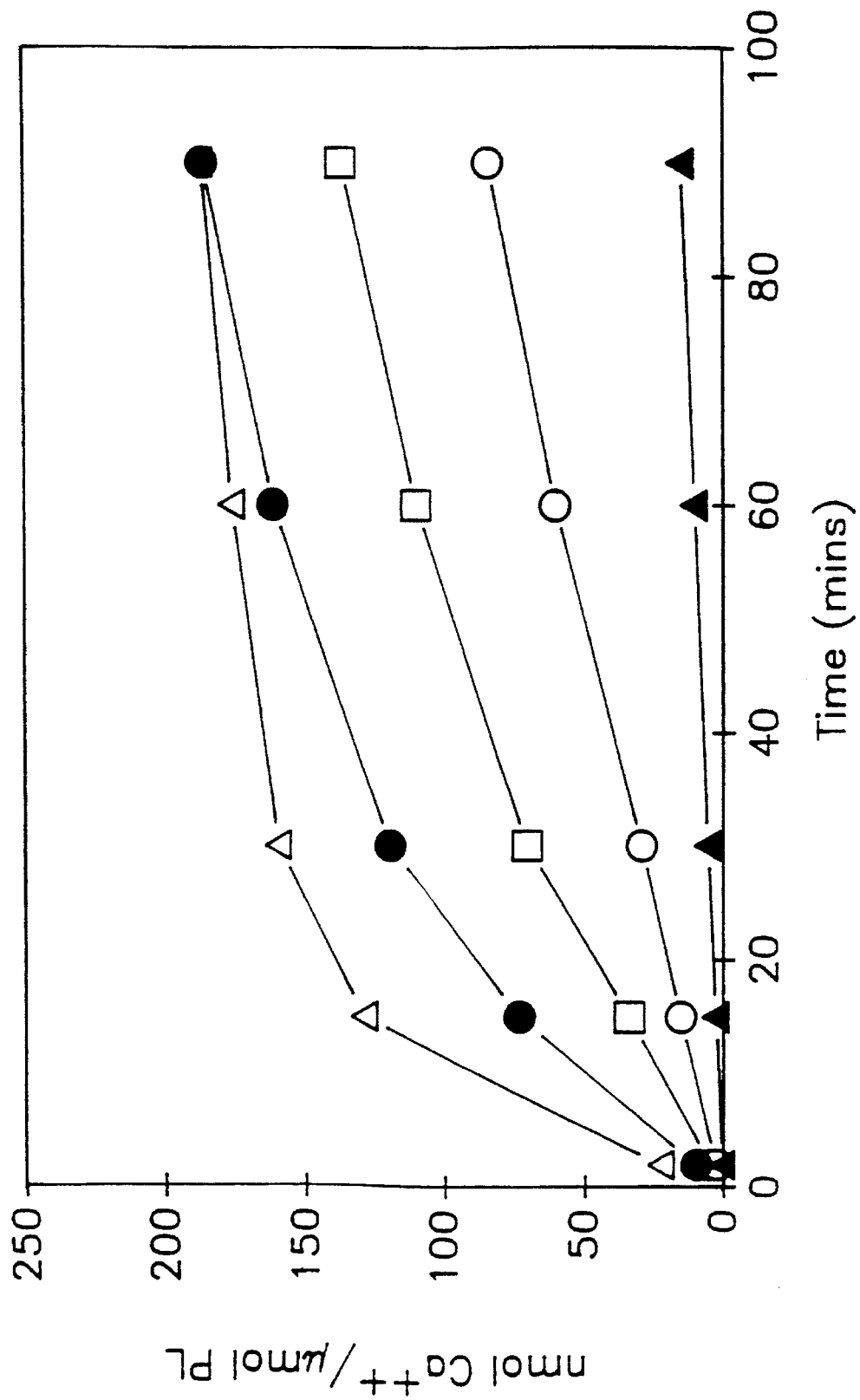
FIG. 7 is a graph depicting the effect of temperature on $Ca^{++}$ accumulation into LUVs in the presence of a pH gradient and A23187 at 15° C. (closed triangle), 26° C. (open circle), 36° C. (open square), 45° C. (closed circle), and 60° C. (open triangle)

The effect of temperature on A23187 mediated $Ca^{++}$ uptake at low A23187 levels (0.05 ug/ml) is shown in FIG. 7. More than trapping efficiency was obtained after two hours at 60° C. The temperature dependence of the initial rate for transport reflected an Arrhenius activation energy of 12.8 Kcal/mol. This activation energy indicates that even with a significant reduction in the amount of ionophore, high cation uptake levels may still be rapidly achieved provided the temperature is elevated.

Comparative Example 1

No pH Gradient

Figure 8:
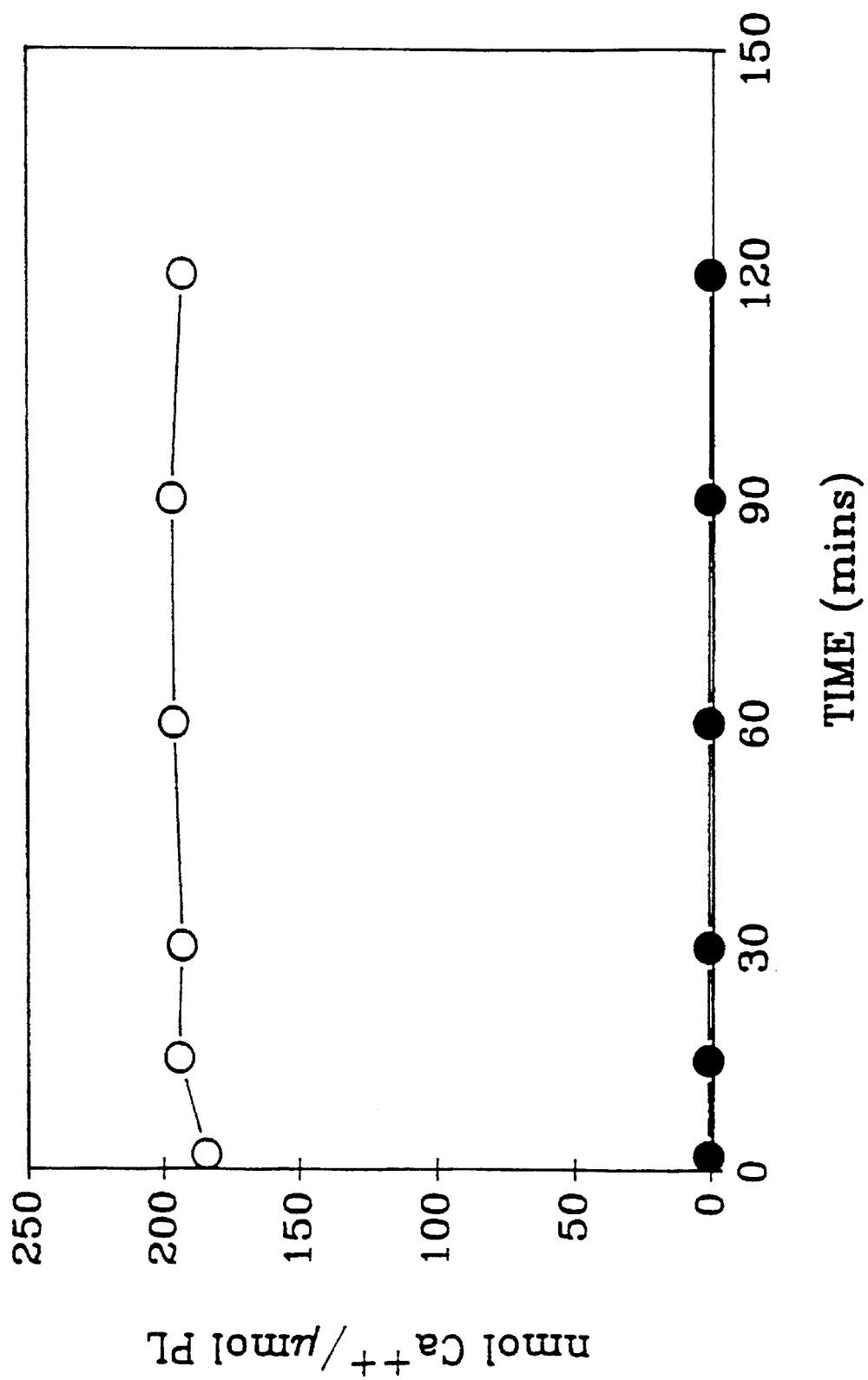
FIG. 8 is a graph depicting the effect of internal buffer on the A23187 mediated accumulation of $Ca^{++}$ in the absence of a transmembrane pH gradient in and out with 300 mM citrate (closed circle) and 300 mM EDTA (open circle)

Mauk and Gamble, *Analytical Biochemistry*, 94, 302–307 (1979) have previously demonstrated that with the presence of a suitable chelator (e.g. nitrilotriacetic acid and EDTA) in the vesicle interior (in the absence of a transmembrane pH gradient), the binding of the A23187 transported cation to the chelator acts as a sufficient driving force for net mediated cation uptake, giving over 90% trapping efficiency. In order to distinguish between this trapping procedure and uptake due to the transmembrane pH gradient, experiments were conducted in the absence of a pH gradient (pH 7.4 in and out) and the presence of citrate (300 mm) or EDTA (300 mm) in the vesicle interior. FIG. 8 illustrates that citrate, unlike EDTA, lacks the ability to act as a driving force for the loading of $Ca^{++}$ a into A23187 containing vesicles. This inability indicates that citrate is not a sufficiently strong chelating agent to drive uptake.

EXAMPLE 2

Enhancement of Iron (Fe2+uptake

EPC and the ionophore A23187 were obtained as before. All other reagents were analytical grade or equivalent.

Large unilamellar vesicles were produced by extrusion, Hope et al., *BBA* 812, 55–65 (1985) using 50 mg of EPC suspended into 1 mL of 300 mM titrate at pH 4.0, of frozen and thawed lipid dispersions through 0.1 um polycarbonate filters (Nuclepore) employing an extrusion device (Lipex Biomembranes, Vancouver). The resulting LUVs were 108 nm in diameter as calculated by a NICOMP particle sizer.

The LUVs, having a pH of 4.0, were then passed down a 10 cm Sephadex G-50 (medium) column previously equilibrated with 300 mM NaCl, 20 mM Hepes (pH 7.5) (Hepes buffered, HBS) to generate the 7.5/4.0 (exterior/interior) pH gradient.

The calcium ionophore, A23187, was initially made up in chloroform. The chloroform was subsequently removed under a stream of nitrogen. The A23187 was used at a concentration of 10 ug/ml. There was added 1.1000 ml of 300 mM NaCl, 20 mM Hepes and 10 mM ascorbate (pH 7.5)

to 0.150 ml of 10 mM $FeSO_4$. $Fe^{++}$ samples were maintained in the reduced state by the addition of ascorbate (10 mM) to the buffers used and by gassing of the buffers with $N_2$ gas to minimize oxidation. Uptake of $Fe^{++}$ was initiated by the addition of 0.250 ml of LUVs (7.5/4.0) to this mixture. There were sampled, when necessary, 0.150 ml aliquots by passing them twice down 1.0 ml Sephadex G-50 columns (dry). These columns were spun for one minute at 2500 rpm in a clinical centrifuge to remove untrapped iron. All experiments were conducted at 23° C. unless stated otherwise.

Table 1 shows the effect of substituting EDTA for titrate as the chelator for iron. This substitution was done to establish whether the presence of a chelator or the transmembrane pH gradient acted as the driving force for iron uptake. The results indicate that neither EDTA nor titrate (both 300 mM) can act as the driving force for significant uptake of iron without the presence of a pH gradient.

Entrapment of the chelator EDTA with no transmembrane pH gradient showed much less accumulation of iron than with the use of a pH gradient (Table 1). Hence, use of a transmembrane pH gradient with some form of chelator (eg. titrate or EDTA) appears to be the best method developed so far for the entrapment of iron, as well as other divalent cations, in liposomes. The A23187 is believed to serve in these systems as an exchange carrier of iron for protons across the phospholipid membrane.

In analyzing the results, all iron concentrations given were adjusted for any background uptake/binding observed for the following controls: pH 7.5/7.5 + A23187; pH 4.0/4.0 + A23187; pH 7.5/4.0 (no ionophore); pH 7.5/7.5 (no ionophore); pH 4.0/4.0 (no ionophore). In general, the pH 7.5/7.5 + A23187 control gave the highest background value observed (less than 15% of the uptake observed for the pH 7.5/4.0 A23187 samples).

Figure 9:
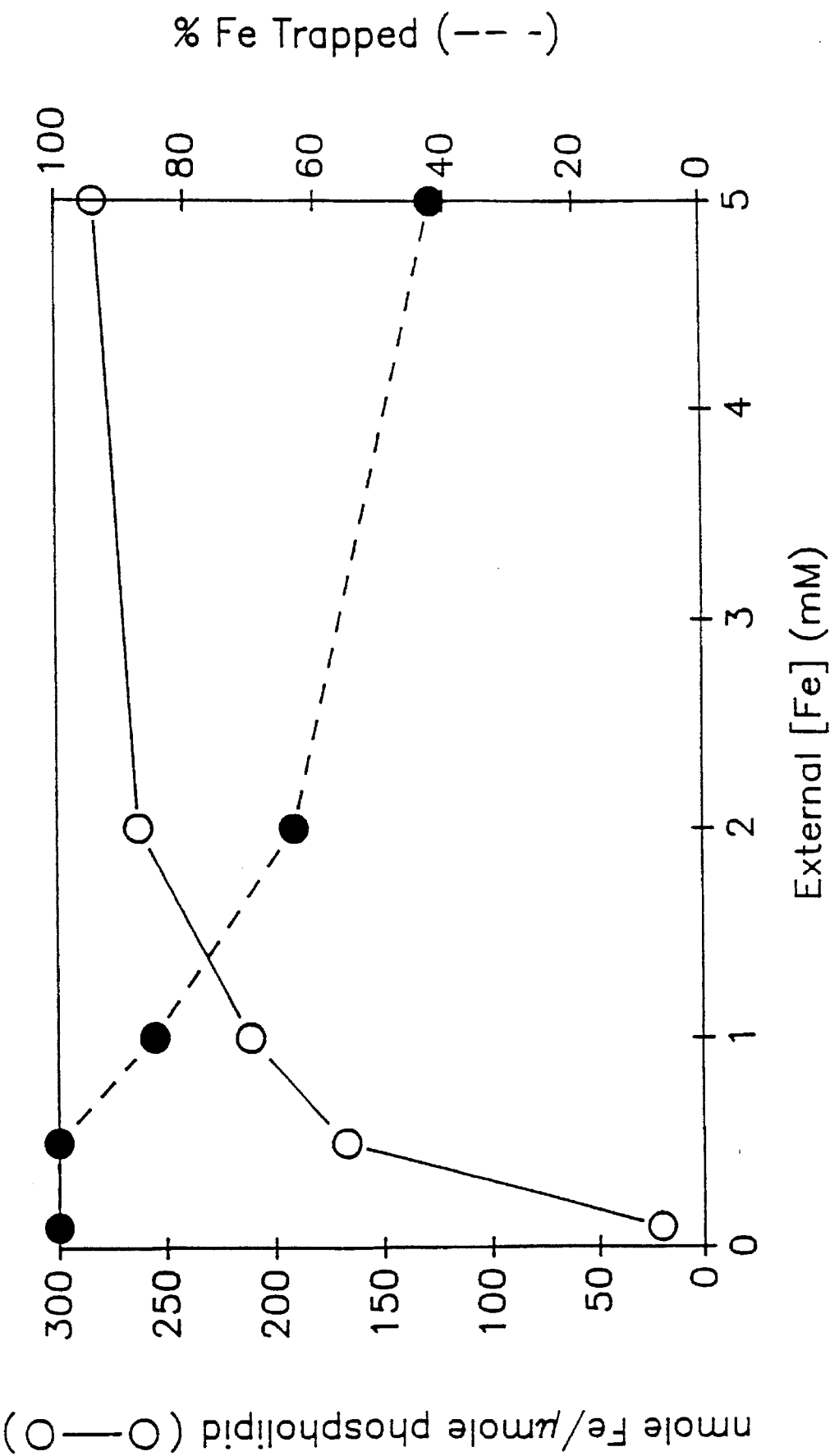
FIG. 9 is a graph depicting the effect of varying external iron concentration on the total amount of iron accumulated (open circles) in EPC vesicles and the trapping efficiency (closed circle)

As illustrated in FIG. 9, as the concentrations of iron increased, the amount of iron entrapped was likewise increased. However, the trapping efficiency of the LUVs decreased dramatically at higher iron concentrations (above 1.0 mM). Hence it was decided to use 1.0 mM iron as the standard concentration for future experiments.

Figure 10:
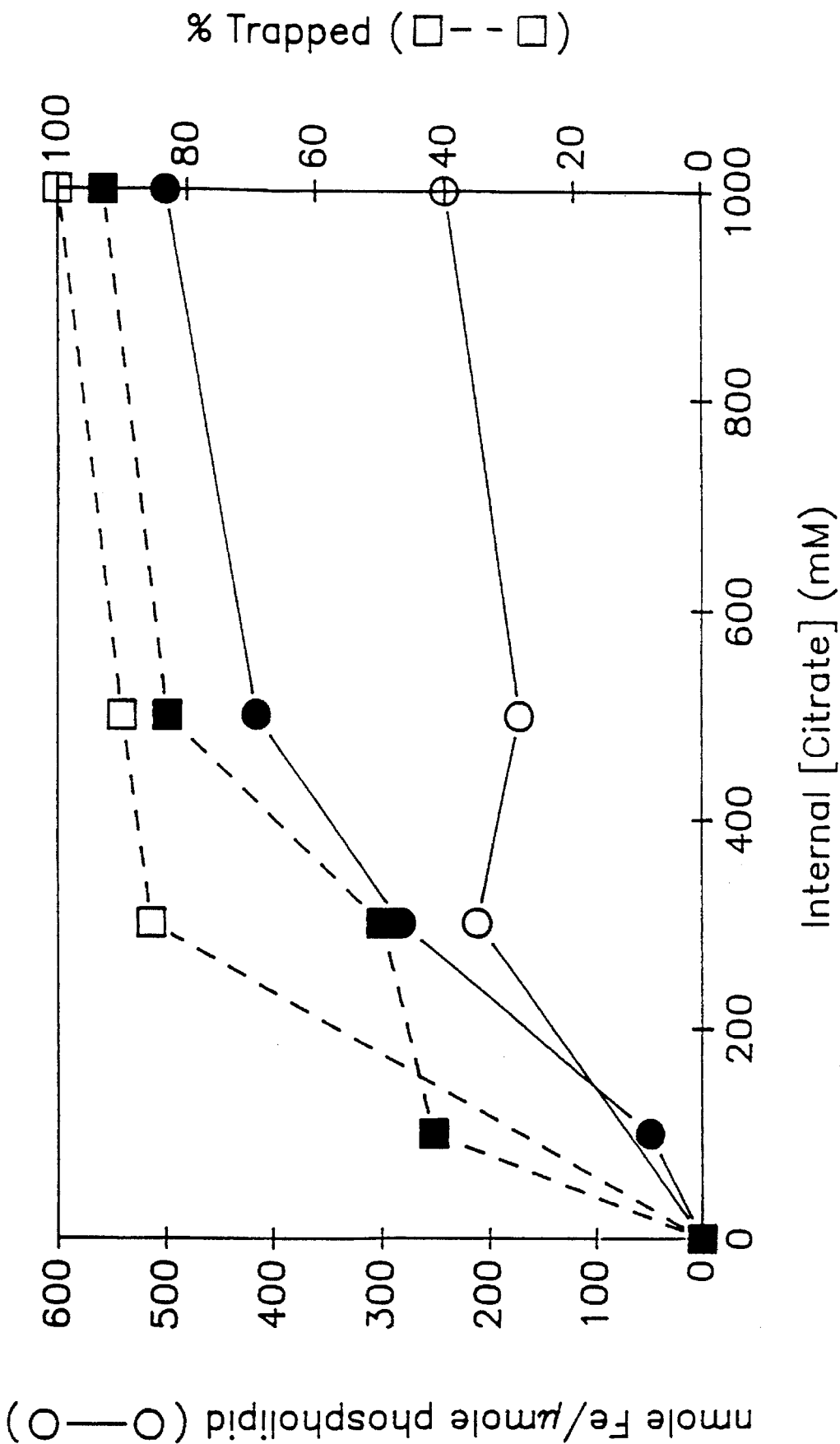
FIG. 10 is a graph depicting the effect of varying the internal citrate concentration on the amount of iron cation accumulated by EPC vesicles (open circle) and the trapping efficiency (closed square) wherein external concentrations of 1.0 (open square and open circle) and 5.0 (closed square and closed circle) mM iron were both tested in the presence of A23187.

As shown in FIG. 10, the amount of iron entrapped increased significantly as the buffering capacity of the titrate was increased up to 300 mM. Subsequent increases in buffering capacity yielded lesser increases in the total amount of iron entrapped. The trapping efficiencies of iron followed the same pattern as that of the total amount of iron entrapped, with a plateau in the trapping efficiency being observed at 300 mM titrate.

Experiments were also undertaken to establish the maximum amounts of iron could be entrapped using this system. The highest amount of uptake (approximately 2300 nmoles iron/umol phospholipid) was observed for LUVs containing 1.75 M titrate with 10 mM external iron.

Increasing the magnitude of the initial transmembrane pH gradient (3.0 pH units) resulted in no significant increase in the amount of iron entrapped. The gradients were increased in both the acidic (7.5/3.0) and basic (8.5/4.0) directions. This is consistent with the results of Veiro and Cullis, who found that decreasing the initial transmembrane pH gradient below 3.0 units resulted in reduced trapping efficiency and dissipation of the pH gradient after $Ca^{+2}$ uptake using an identical liposomal system. Use of high titrate concentrations (at least 300 mM) generally results in maintenance of a pH gradient of at least 2.0 units after uptake has taken place.

EXAMPLE 3

Iron (Fe3+) Uptake

Experimental conditions of Example 2 were altered so as to establish whether one specific oxidation state of iron ($Fe^{++}$ or $Fe^{3+}$) was responsible for the background binding and transport processes observed. $Fe^{3+}$ samples were obtained from $FeCl_3$.

Experiments investigating the effects of the oxidation state on the transport of iron found that the ferrous (+2) state of iron was the form that was transported across (336 Moles Fe/umol phospholipid). The ferric (+3) state of iron was hardly transported at all (47 Moles Fe/umol phospholipid). This observation is in agreement with those of Young and Gomperts (Young, S. P. and Gomperts, B. D. 1977, Mobile carrier ionophores for Fe(II), Biochem. Biophys. Acta 469:281) who also found that A23187 was capable of transferring Fe (II) but not Fe (III).

EXAMPLE 4

Centrifugation of Iron-Containing Vesicles

The experiments involving the centrifugation of the iron-liposomes made use of LUVs made according to Example 2 but which were extruded through 200 nm pore size filters. The resulting vesicles were approximately 214 nm in diameter, as calculated by a NICOMP particle sizer. The vesicles had 1.0M citrate as the internal buffer and were incubated with 10 mM Fe (either $Fe^{++}$ Fe3+). The iron-liposomes were spun at 4° C. using 15,000×g in an Eppendorf microcentrifuge.

Iron was assayed spectrophotometrically using bathophenanthroline sulfonate. Pippard, M. J. and Stray, S. 1982. "Simple assay for urinary iron after desferrioxamine therapy". A.J.C.P. 77: 324. There were added to 0.050 ml of the sample to be assayed 0,250 ml of 3.3M sodium acetate (pH 4.7), 0.100 ml of 5.0 % Triton X-100, 0.050 ml of 0.2% (w/v) bathophenanthroline sulfonate in 1.0 % thioglycolic acid and 0.550 ml of water (total volume=1.000 ml). The reaction was allowed to proceed for at least 15 minutes before the resulting red color was measured at 535 nm using a Shimadzu UV-160 spectrophotometer.

Phospholipid concentrations were calculated by a modification of the method of Fiske and Subbarow, referenced earlier.

Table 2 shows the distribution of liposomes which have been centrifuged to pellet the "heavy liposomes." Spinning down of the liposomes after incubation with iron resulted in a visible pellet after 25 minutes at about 15 000× g (using an Eppendorf micro-centrifuge). The pellet and supernatant were easily separated. A large percentage (46.5%) of the total number of liposomes are spun down. Control liposomes (containing no iron) of the same size produced a pellet containing only 15.0% of the total lipid. This value was subtracted from the obtained for the iron-liposomes to calculate the net increase in the percentage of liposomes that pelleted (31.5%).

TABLE 1

Comparison of EDTA and Citrate as Iron-Chelators

| | nmoles Fe/umole phospholipid | |
|---|---|---|
| Experimental Conditions | EDTA | Citrate |
| 7.5/4.0 + A23187 | 835 ± 39 | 1660 ± 193 |
| Controls | | |
| 7.5/7.5 + A23187 | 62 ± 7 | 214 ± 6 |
| 4.0/4.0 + A23187 | 41 ± 6 | 180 ± 3 |
| 7.5/4.0 | 222 ± 19 | 11 ± 6 |
| 7.5/7.5 | 71 ± 18 | 40 ± 17 |
| 4.0/4.0 | 56 ± 4 | 29 ± 11 |

All values are means ± SEM, n=3. The reactions were run for 1 hour at 23° C. using 5.0 mM external iron and 1.0M internal citrate. Samples were passed down two spun-columns to remove any free iron remaining. All liposomes employed were extruded through 100 nm filters in the LUVET process.

TABLE 2

Effect of Centrifugation of Iron-Liposomes

| | Supernatant | Pellet |
|---|---|---|
| Total Lipid | 53.5% ± 5.9% | 46.5% ± 5.3% |
| Total Lipid-Controls | 85.0% ± 3.6% | 15.0% ± 2.6% |
| Total Iron | 34.6% ± 3.6% | 65.4% ± 7.3% |
| nmoles Fe/umole Lipid | 1260 ± 60 | 2740 ± 170 |
| Particle Diameter (nm) | 214 ± 73 | 214 ± 73 |

Fe uptake reactions were run for 2 hours at 23° C. with 2.0 mM external iron and 1.0M internal citrate, n=3.

All liposomes employed were extruded through 200 nm filters in the LUVET process.

What is claimed is:

1. A method for entrapment of a cation in a vesicle having a membrane and an acidic aqueous compartment comprising the step of contacting the vesicle with a buffer solution comprising the cation and a lipophilic, ionophoretic antibiotic capable of complexing with the cation and increasing the cation's permeability across the vesicle membrane, wherein there is a pH gradient between the acidic aqueous compartment and the buffer solution wherein the buffer solution is free of chelating agents and wherein at least about 99% of the cation originally available external to the vesicle is entrapped in the vesicle.

2. The method of claim 1 wherein said vesicle is a unilamellar vesicle.

3. The method of claim 2 wherein said vesicle is a large unilamellar vesicle.

4. The method of claim 1 wherein said acidic aqueous compartment has a pH between about 3 and 6.

5. The method of claim 4 wherein said acidic aqueous compartment has a pH between about 4 and 4.5.

6. The method of claim 1 wherein said pH gradient is above about 3.

7. The method of claim 6 wherein said pH gradient is between about 3.0 and 3.5.

8. The method of claim 1 wherein said ionophoretic antibiotic is A23187, desferrioxamine, ionomycin, lasalocid A, or A-204.

9. The method of claim 1 wherein said cation is calcium, iron, barium, gold, gadolinium, gallium or indium.

10. A method for entrapment of $Ca^{++}$ in a vesicle having a membrane, a transmembrane pH gradient and an internal aqueous compartment comprising citrate solution at about pH 4.0, comprising contacting the vesicle with a buffer solution comprising the $Ca^{++}$ and the ionophore A23187, wherein the buffer solution is free of chelating agents and wherein at least about 99% of the cation originally available external to the vesicle is entrapped in the vesicle.

11. The method of claim 10 wherein the vesicle is a unilamellar vesicle.

12. The method of claim 11 wherein the vesicle is a large unilamellar vesicle.

13. A method for entrapment of $Fe^{++}$ in a vesicle having a membrane, a transmembrane pH gradient and an internal aqueous compartment comprising citrate solution at about pH 4.0, comprising contacting the vesicle with a buffer solution comprising the $Fe^{++}$ and the ionophore A23187 wherein the buffer solution is free of chelating agents and wherein at least about 99% of the cation originally available external to the vesicle is entrapped in the vesicle.

14. The method of claim 13 wherein the vesicle is a unilamellar vesicle.

15. The method of claim 14 wherein the vesicle is a large unilamellar vesicle.

\* \* \* \* \*